United States Patent [19]

Merickel et al.

[11] Patent Number: 4,945,478

[45] Date of Patent: Jul. 31, 1990

[54] NONINVASIVE MEDICAL IMAGING SYSTEM AND METHOD FOR THE IDENTIFICATION AND 3-D DISPLAY OF ATHEROSCLEROSIS AND THE LIKE

[75] Inventors: Michael B. Merickel; Charles S. Carman; James R. Brookeman; John P. Mugler, III; Carlos R. Ayers, all of Charlottesville, Va.

[73] Assignee: Center for Innovative Technology, Herndon, Va.

[21] Appl. No.: 117,508

[22] Filed: Nov. 6, 1987

[51] Int. Cl.$^5$ .............................................. G06F 15/70
[52] U.S. Cl. .................................... 364/413.22; 382/6
[58] Field of Search ...................... 364/413.19, 413.22, 364/413.13, 521, 522; 340/729; 382/9, 6, 15, 22; 324/309

[56] References Cited

U.S. PATENT DOCUMENTS

| | | | |
|---|---|---|---|
| 4,083,232 | 4/1978 | Heyser et al. | 73/618 |
| 4,477,777 | 10/1984 | Gordon | 324/307 X |
| 4,573,014 | 2/1986 | Riederer | 324/307 |
| 4,710,876 | 12/1987 | Cline et al. | 364/414 |
| 4,737,921 | 4/1988 | Goldwasser et al. | 364/521 |
| 4,741,043 | 4/1988 | Bacus | 364/413.13 X |
| 4,751,643 | 6/1988 | Lorensen et al. | 364/413.13 |

OTHER PUBLICATIONS

Udupa, J., "Interactive Segmentation and Boundary Surface Formation for 3-D Digital Images", Computer Graphics and Image Processing 18, pp. 213-235 (1982).
Udupa, J, "Display of 3D Information in Discrete 3D Scenes Produced by Computerized Tomography", Proceedings of IEEE, vol. 71, No. 3, Mar., 1983, pp. 420-431.
Tuy, H. et al., "Direct 2-D Display of 3-D Objects", IEEE, Oct., 1984.
"MR Imaging of the Aorta with Three-Dimensional Vessel Reconstruction; Validation by Angiography", Valk et al., Radiology, vol. 157, pp. 721-725, Dec., 1985.
"Magnetic Resonance Imaging of Aortic Disease; Preliminary Results", Amparo et al., AJR, vol. 143, pp. 1203-1209, Dec. 1984.
"Nuclear Magnetic Resonance Imaging of Atherosclerotic Disease" Herfkens et al., Radiology, vol. 148, pp. 161-166, Jul. 1983.
"Technical Development and Instrumentation", Vannier et al., Radiology, vol. 154, pp. 221-224.
"Evaluation of NMR Imaging for Detection and Quantification of Obstructions in Vessels", Kaufman et al., Investigative Radiology, vol. 17, Nov.-Dec. 1982, pp. 554-560.
"Pattern Recognition for Tissue Characterization in Magnetic Resonance Imaging", Koenig et al., Health Care Instrumentation, pp. 184-187.
"Quantification of Atherosclerosis with MRI", Merickel et al., 39th ACEMB, Marriott Hunt Valley Inn, Baltimore, MD Sep. Sep., 13-16, 1986, p. 358.
"Color 3-D Imaging of Normal and Pathologic Intracranial Structures", IEEE CG&A, Sep., 1984, pp. 5-17.
"Magnetic Resonance Imaging: Filling a New Diagnostic Role", Burnett, Photonics Spectra, Oct., 1986.
"Multispectral Magnetic Resonance Image Analysis," Vannier et al., CRC Critical Reviews in Biomedical Engineering, pp. 117-144.
"MR Imaging of Blood Vessels Using Three-Dimensional Reconstruction: Methodology," Hale et al., Radiology, vol. 157, No. 3, pp. 727-733.
"Three-Dimensional Display of Blood Vessels in Magnetic Resonance Imaging," Rossnick et al., Health Care Instrumentation, Oct. 7-10, 1986, pp. 201-204.

Primary Examiner—Charles E. Atkinson
Assistant Examiner—Steve Kilby
Attorney, Agent, or Firm—Staas & Halsey

[57] ABSTRACT

There is disclosed an image processing, pattern recognition and computer graphics system and method for the noninvasive identification and evaluation of atheroscelerosis using multidimensional Magnetic Resonance Imaging (MRI). Functional information, such as plaque tissue type, is combined with structure information, represented by the 3-D vessel and plaque structure, into a single composite 3-D display. The system and method is performed with the application of unsupervised pattern recognition techniques and rapid 3-D display methods appropriate to the simultaneous display of multiple data classes. The results are a high information content display which aids in the diagnosis and analysis of the atherosclerotic disease process, and permits detailed and quantitative studies to assess the effectiveness of therapies, such as drug, exercise and dietary regimens.

64 Claims, 11 Drawing Sheets

SEGMENTATION #2

SEGMENTATION #3

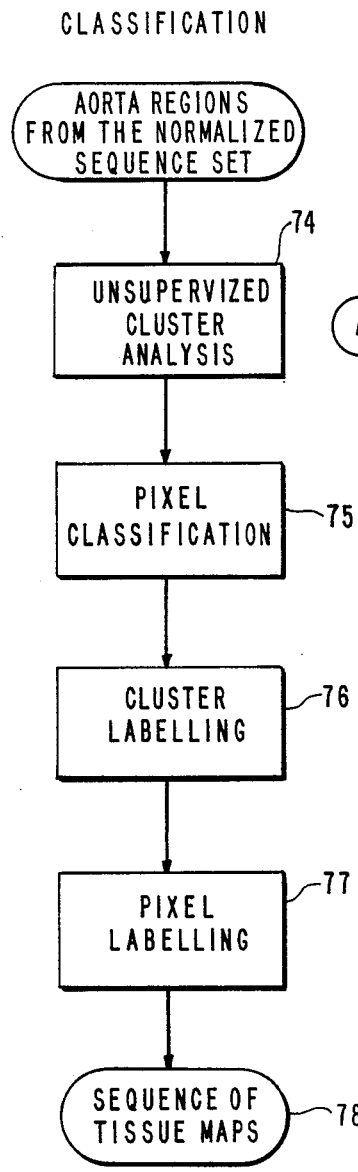
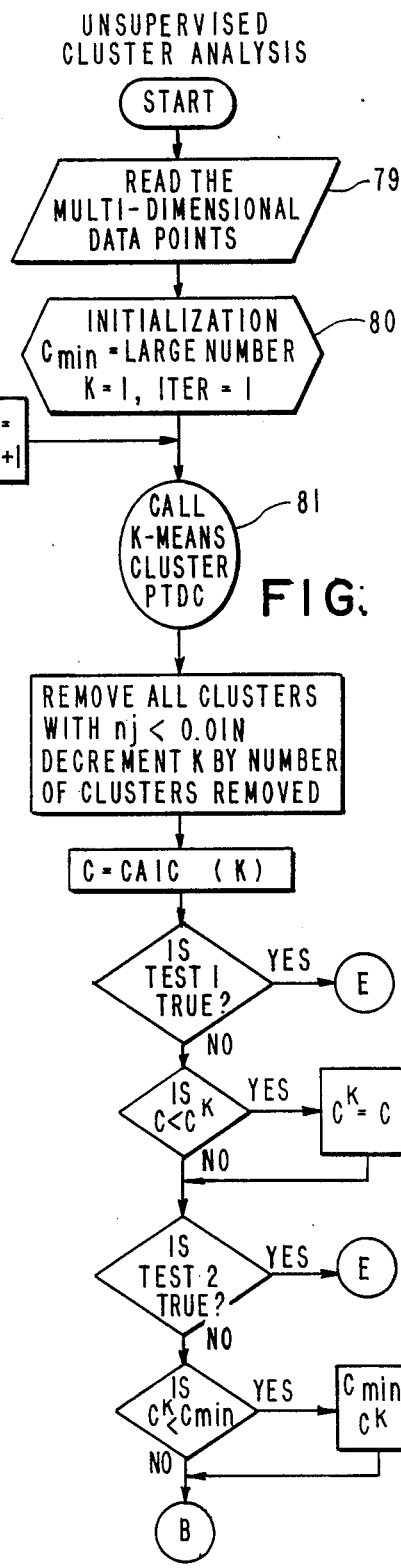
FIG. 16
FIG. 17

3D QUANTIFICATION AND DISPLAY
1. THE INPUT TISSUE IMAGES.
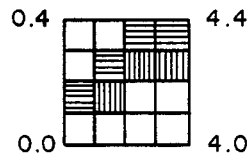
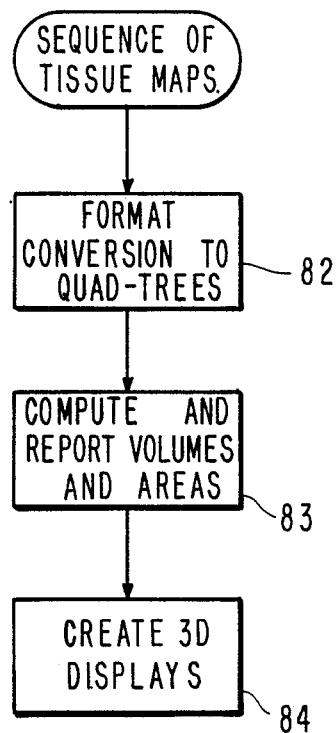
2. ARE CONVERTED TO QUAD TREES.
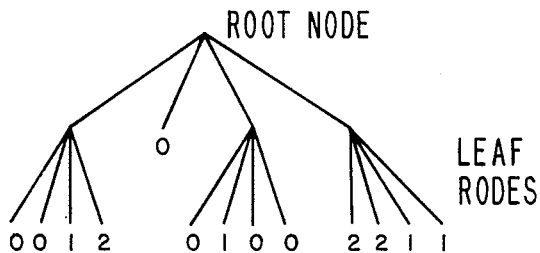
4. THE DISPLAY IS CREATED INTERACTIVELY WITH THE USER; ALLOWING ON-LINE SELECTION OF ROTATION, SCALING, TRANSLATION, CUT-AWAYS, AND SELECTIVE DISPLAY OF SPECIFIC TISSUES.
FIG. 19
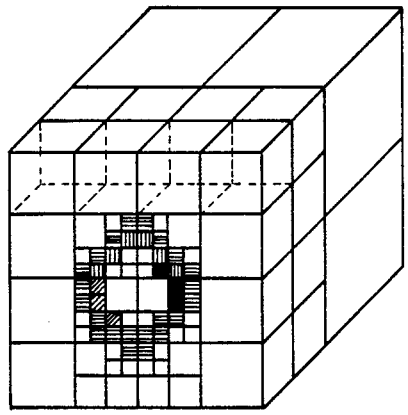

NONINVASIVE MEDICAL IMAGING SYSTEM AND METHOD FOR THE IDENTIFICATION AND 3-D DISPLAY OF ATHEROSCLEROSIS AND THE LIKE

This invention relates to the three dimensional (3-D) display of atherosclerosis and the like which assist in medical evaluation.

Presently, the standard for evaluation of atherosclerosis is angiography. Angiography carries the risk of high exposure to X-rays, reaction to the contrast medium and embolism.

New biomedical imaging modalities, such as Magnetic Resonance Imaging (MRI) and Positron Emission Tomography (PET), are capable of providing both structural as well as functional information regarding biological tissue and associated physiological processes. However, it is currently unclear how to extract, quantify and effectively display this structural and functional information. The present invention involves the development and integration of multidimensional image processing, pattern recognition and 3-D display techniques which are capable of effectively combining this structural and functional information into a single 3-D high information content display. As used herein, a picture or computer screen which is actually two dimensional (2-D) is considered 3-D when the display appears to be 3-D such as a perspective view. It uses a pattern recognition and graphical display system for noninvasively evaluating atherosclerosis based upon multiple pulse sequence MRI image input.

These pattern recognition and 3-D display techniques use MRI for noninvasively quantifying and evaluating atherosclerosis. Cardiovascular disease due to atherosclerosis is a leading cause of death in the United States. The diagnosis and management of the consequences of atherosclerosis is a major contributing factor to health care costs. Atherosclerosis is typically detected only after the occurrence of serious or catastrophic events such as stroke, myocardial infarction, or peripheral vascular ischemia.

Work by others has demonstrated that different pulse sequences are able to enhance the contrast between certain atherosclerotic tissue types (L. Kaufman, L. E. Crooks, P. E. Sheldon, et al, "Evaluation of NMR Imaging for Detection and Quantification of Obstructions in Vessels", Invest. Radiol., vol. 17, pp. 554–560, Nov.-Dec. 1982; R. J. Herfkens, C. B. Higgins, H. Hricak et al, "Nuclear Magnetic Resonance Imaging of Atherosclerotic Disease", Radiology, vol. 48, pp. 161–166, July 1983; and G. E. Wesbey, C. B. Higgins et al, "Magnetic Resonance Applications in Atherosclerotic Vascular Disease", Cardiovascular and Interventional Radiology, vol. 8, pp. 342–350, 1986.) The present invention uses multidimensional pattern recognition techniques that combine information from different pulse sequences to provide more discrimination than available with single pulse sequences. The present invention automatically identifies the different atherosclerotic tissue class types involved in the disease process for both protrusional as well as non-protrusional lesions with identification of different tissue types. This permits the stage of the disease process to be evaluated by the noninvasive evaluation of atherosclerosis in patients.

The invention distinguishes the tissue classes of normal muscle wall (i.e., intima and media) from major atheromatous plaque constituents, including fatty lipid containing plaque, thrombus, fibrous connective tissue and calcified plaque and combines functional information, such as plaque type, with structural information, represented by the 3-D vessel structure, into a single composite 3-D display.

The ability to quantitatively evaluate a disease such as atherosclerosis requires combining together structural information as well as functional information. Structural information represents characteristics of the vessel such as the 3-D shape of the vessel and its overall organization (i.e., location of vessel bifurcation and branching; and the degree of vessel occlusion represented by quantification of vessel narrowing. Functional information, involves identification and quantitative volume measurement of soft tissue types involved in the disease process which provide information regarding the physiological stage of the disease.

Various objects and advantages of this invention will become apparent by reference to the following description including the accompanying drawings, in which:

FIG. 16 shows a flow diagram of the classification steps;

FIGS. 17 and 18 shows a flow chart of the unsupervised cluster analysis;

FIG. 19 shows a flow chart of the 3-D quantification and display and a quad tree representation of volume surrounding a vessel (e.g., aorta) located in the center of the cube with long axis pointing towards the front face of the cube.

Figure 1:
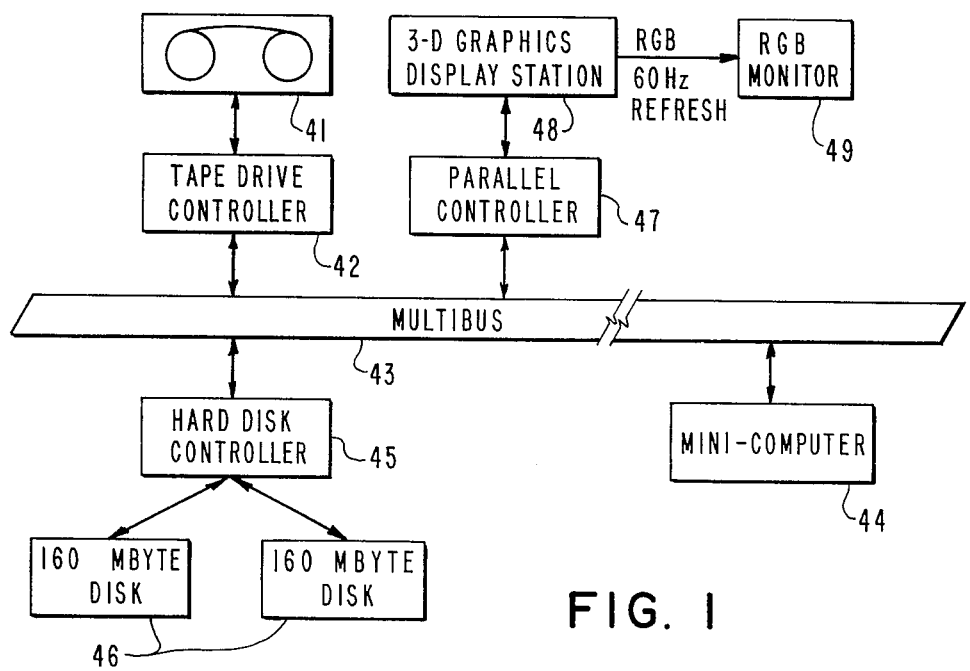
FIG. 1 shows a block diagram of the components of the apparatus used in the invention.

With reference to FIG. 1, there is shown a block diagram of the major components of the apparatus used in the invention. A Siemens 1 Tesla Magnetom Imager with Siemens software, including reconstruction software, available from Siemens Medical System Inc., 186

Wood Avenue, South Iselin, N.J. 08830 is utilized to noninvasively obtain information for imaging the aorta. This is done using a surface coil as is well known in the practice of MRI technology. The MRI operations obtains a set of three transverse images (proton density or pd, $T_1$ and $T_2$ "weighted" images) for each of approximately ten different slice positions. The data is then transferred to this invention using a magnetic tape and a tape drive 41 of FIG. 1.

The standard spin-warp imaging method is utilized with spin-echo pulse sequences. In MRI, the time between the excitation pulse and the spin-echo maximum is denoted as TE, and the repetition time between serial excitation pulses is referred to as TR. Values of TE and TR for emphasizing differences in proton density, $T_1$ and $T_2$ are listed elsewhere. Images emphasizing differences in proton density are obtained using relatively short values of TE and long values of TR to obtain maximum signal intensity. Images emphasizing differences in $T_1$, the spin lattice relaxation time, are obtain using relatively short values of TR and TE. Images emphasizing differences in $T_2$, the spin-spin relaxation time, corresponding to long values of TE and long TR times to allow equilibrium between scans. Such $T_2$ weighted images are usually obtained as the second echo of a dual echo sequence.

The complete sets of corresponding $T_1$, pd and $T_2$ imagery are written onto a standard nine-track magnetic tape at the MRI facility at a density of 1600 bits per inch. The tape is then placed in the tape drive 41 of FIG. 1 which is operated by tape drive control 42 to supply information to a multi-bus 43 in a well known manner. The multi-bus connects the minicomputer 44 which is a Masscomp MC-5520 with two megabytes of memory, 400 megabytes of disk storage, Unix real time operating system and a tape drive. The computer is available from Masscomp, 1 Technology Park, Westford, Mass. 01886. Also connected to the multi-bus through a standard hard disk controller 45 are two 160 megabyte hard disk storage devices 46. Still further connected to the multi-bus by means of a parallel controller 47 is the 3-D graphics display station 48 driving an RGB monitor 49 with an RGB 60 hertz refresh. The display station is a LEX 90/35 Model 2.2 with Solid View firmware and is available from Lexidata Corporation, 755 Middlesix Turnpike, Billerita, Mass. 01865. The computer operations can be integrated into a single unit rather than distributed between the minicomputer and graphics display station.

Figure 2:
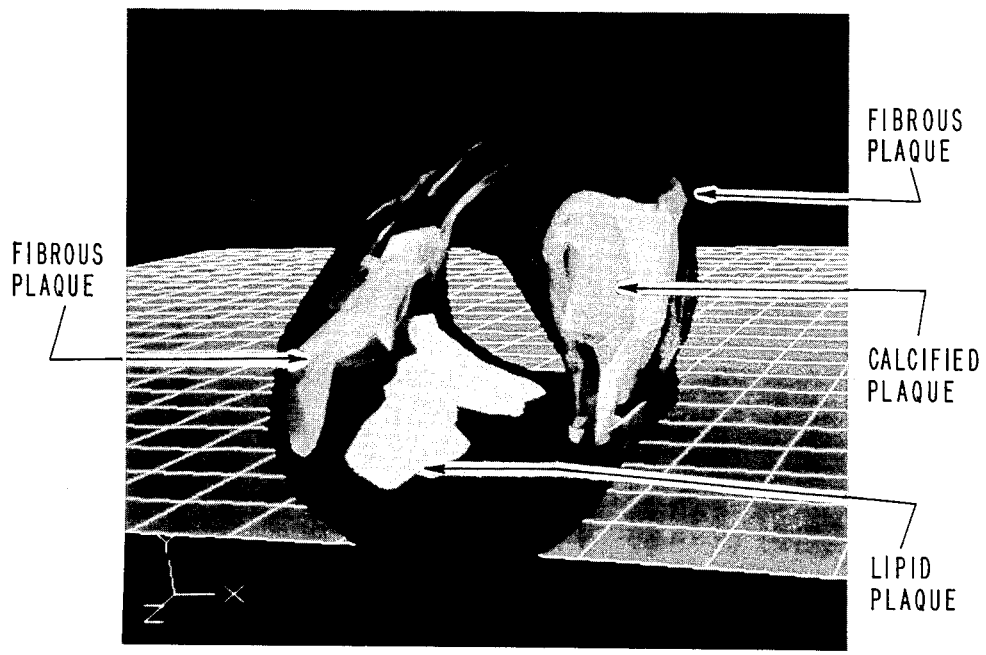
FIG. 2 shows a perspective computer image of a portion of a human aorta with the various soft tissues in contrasting grays representing color in the original.
Figure 8:
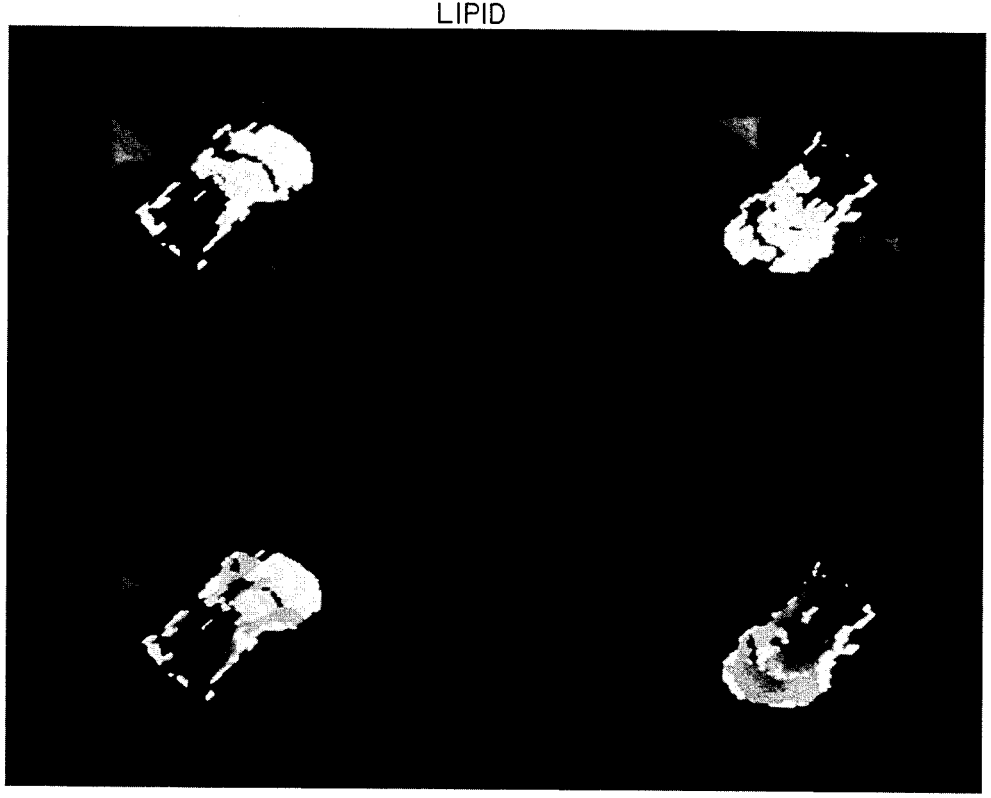
FIG. 8 shows four 3-D views of a diseased aorta.
Figure 9:
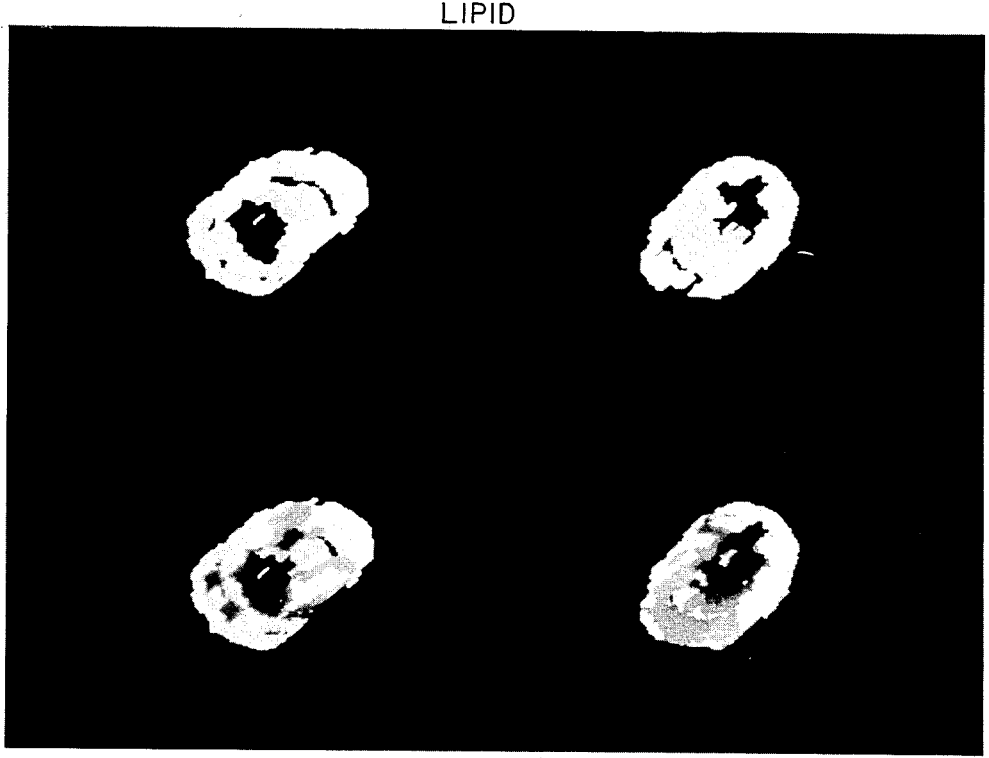
FIG. 9 shows a view similar to FIG. 9 except for omission of the background.

With reference to FIG. 2, there is shown a black and white perspective computer image of a portion of a human aorta. The actual image is in color with the fibrous plaque being green, the lipid plaque being yellow and the calcified plaque being red. The black tubular portion represents the normal muscle wall of a vessel. This particular image was created in part manually as a final step of the invention since the software and hardware for this final step, because of its expense, is not yet available to the inventors. However, except for this final part, the rest of the operation is automatic as will be seen more fully with the following description. The perspective view of FIGS. 8 and 9 depict similar information and were created automatically with equipment available to the inventors.

Figure 3:
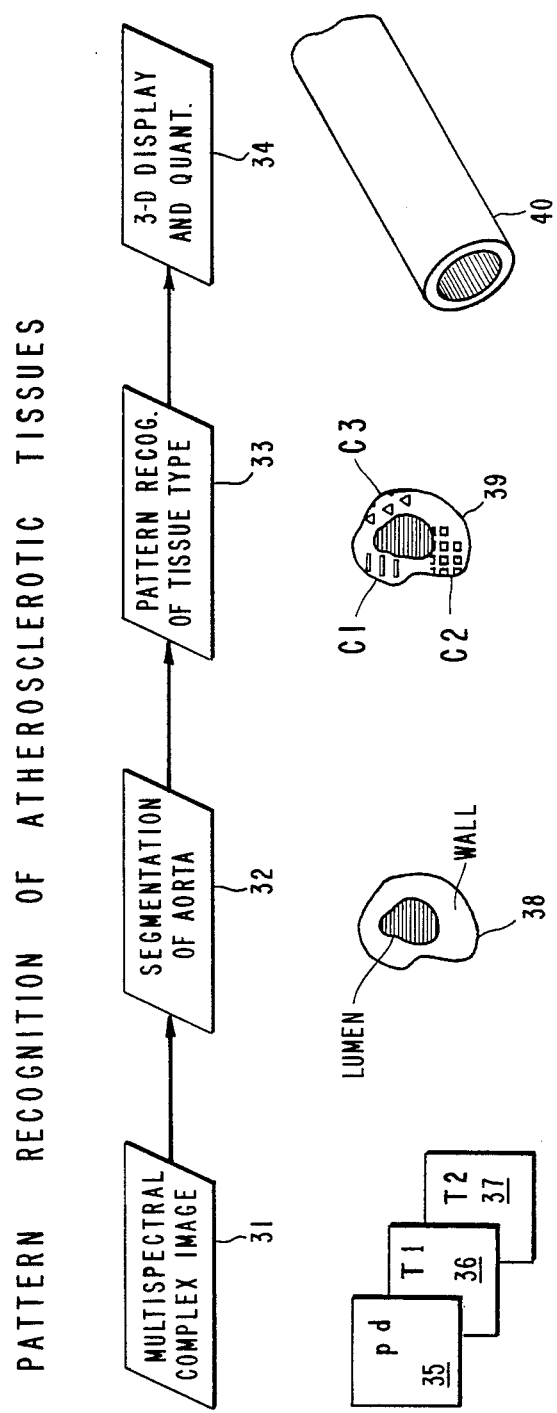
FIG. 3 shows an overall flow chart of the pattern recognition of atherosclerotic tissues.

The image processing system of the present invention determines correlated structural and functional information of atherosclerosis which is shown in block diagram form in FIG. 3. The major steps in the process are:

(1) Inputting the system multiple pulse sequence images 3 (usually portion density (pd) 35, $T_1$ 36 and $T_2$ 37 well known in MRI) of a major vessel taken in cross section. (2) Segmenting the entire scene to extract the major vessel(s) of interest from the rest of the scene 32. (3) Identification of the inner and outer wall boundaries of the major vessel using contour extraction methods to identify the vessel wall 38; (4) Classification of the different soft tissue types of interest using pattern recognition 33 in the vessel wall identified in (3) above. (5) Creating a 3-D data base for display and quantification for the different soft tissue types 34 which is shown as a display 40 using 3-D graphical techniques. Steps (2) and (3) involve determination of the vessel wall boundaries and can therefore be considered determinative of most of the structural information. Steps (4) and (5) involve classification of the tissues in the vessel wall and creation of a 3-D data base of the resulting class types as shown in 39 (e.g., "normal wall" and the major atheromatous plaque constituents of fatty plaque C2, fibrous plaque C1, and complex plaque with possible calcification C3). The identification of these soft tissue types represents the functional information because it can be directly utilized for evaluation of the physiological stage of the disease. This is done by examination of the ratios of the various plaque constituent volumes to the total wall volume.

The output of the pattern recognition procedure is a sequence of 2-D image slices in which each pixel has been replaced by a class number denoting the tissue type to which it has been classified. These 2-D slices form a volume of class numbers (i.e., 3-D array of integers) as shown schematically in the lower right corner of FIG. 19. At the lower right hand corner of FIG. 19, the quadtree representation of volume surrounding a vessel (e.g., aorta) located in the center of the cube with the long axis pointing toward the front face of the cube. The various batch marks indicate quadrants corresponding to different tissue types in a vessel wall. The blank cubes surrounding the aorta are background quadrants. The blank quadrants inside the wall represents the vessel.

The lower abdominal aorta is preferred for in vivo imaging due to its large size as well as the relatively small movement artifacts due to respiration. Images are generated using a Siemens spine coil on a 1 Tesla Siemens Magnetom Imager. The invention utilizes transverse $T_1$, proton density (pd) and $T_2$ weighted images which are obtained from approximately 10 different slice positions. The examples used are a patient with confirmed advanced atherosclerosis and a "normal" patient with no significant disease. The patient with atherosclerosis was a 63 year old man whose disease had been confirmed clinically and by prior angiography. The "normal" subject was a 28 year old man with no diagnosed disease.

The raw MRI images contained several artifacts which have to be removed before segmentation and classification can be performed. Most artifacts are caused by the use of the spine coil and are typical of surface coils employed in MRI imaging to increase spatial resolution and the signal to noise ratio. The sensitivity profile of the surface coil, such as the spine coil (not shown but well known in the art) employed in this investigation, causes the average intensity of the image to fall off with distance from the center of the coil. This intensity fall off causes an intensity gradient to occur across the image of an individual slice as well as a reduction in average intensity of slices imaged further from the coil.

The intensity gradient within a slice is reduced by dividing each image by a spatially smoothed copy of itself on a pixel by pixel basis (J. Haselgrove and M. Prammer, "An Algorithm for Compensation of Surface-Coil Images for Sensitivity of the Surface Coil", Magnetic Resonance Imaging, vol. 4, pp. 469-472, 1986). This significantly reduces the low frequency coil surface intensity gradient and produces some high frequency emphasis which enhances the contrast of edges (R. C. Gonzales and P. Wintz, Digital Image Processing, Reading, Mass: Addison-Wesley Publishing, Co., 1977). Note: all publications mentioned are incorporated by references and made a part hereof.

The average intensity of slices fall off with distance from the surface coil which requires all of the slices belonging to each of the 3 pulse sequences to be normalized to some standard. This is accomplished by normalizing each of the sequences to the mean intensity value of a small set of easily identifiable tissues common to all slices. For this data set; skeletal muscle and interstitial tissue is used as the readily identifiable tissues for normalization. The mean values for skeletal and interstitial tissue for each pulse sequence are then used to define the set of standard intensity values for these reference tissues, which then allow computation of the $T_1$, pd and $T_2$ normalization scale factors for each slice.

A third major artifact is whole pixel shifts between the $T_1$, pd and $T_2$ pulse sequences for an individual slice. These pixels shifts are due to a combination of patient movement and configuration of the Siemens reconstruction software. The shifts are corrected by spatially shifting the $T_1$, pd and $T_2$ images until they line up to one another by visual inspection.

Figure 4:
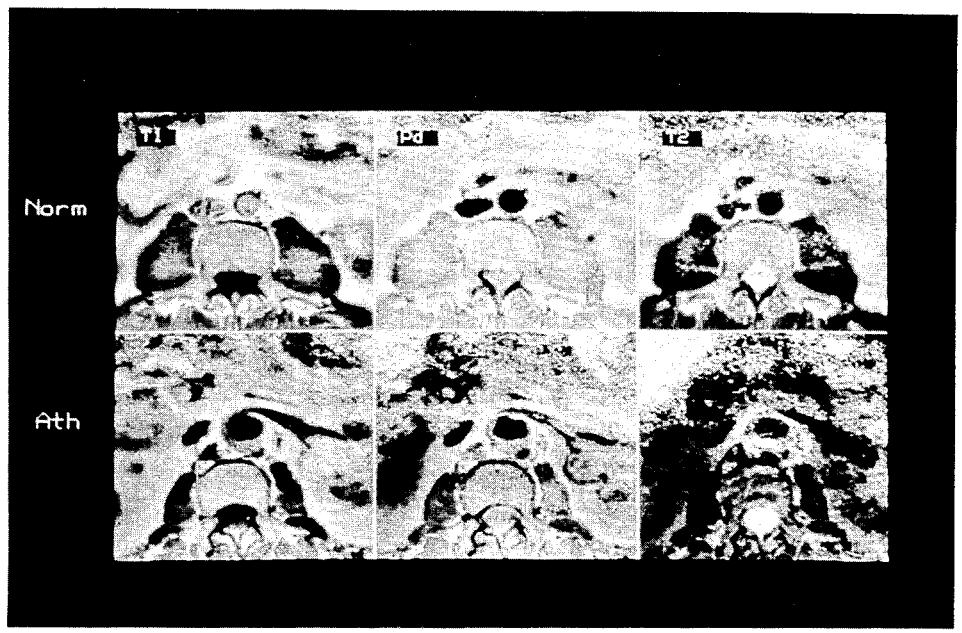
FIG. 4 shows a representative cross sectional $T_1$, pd and $T_2$ images through the lower abdominal aorta in normal subject (Norm, top row) and patient with advanced atherosclerosis (Ath, bottom row)

Some of the basic characteristics of the aorta viewed with MRI are set forth in this and the next paragraph. FIG. 4 shows a set of $T_1$, pd and $T_2$ transverse images through a representative section of the "normal" subject and the patient with advanced disease. The $T_1$ and $T_2$ images through the diseased vessel clearly show the wall of the aorta to be thickened, particularly on the dorsal side next to the vertebral column. The pulse sequence parameters for the "normal" subject are: $T_1$=SE 500/20, pd=SE 1700/32 and $T_2$=SE 1700/64; x-y resolution equals 0.59 mm per pixel; distance between slices equals 15 mm; and slice thickness=10 mm. The parameters for the patient with advanced disease are: $T_1$=SE 900/20, pd=SE 3600/20 and $T_2$=SE 3600/60; x-y resolution equals 0.59 mm per pixel; distance between slices equals 10 mm; and slice thickness equals 5 mm.

Figure 5:
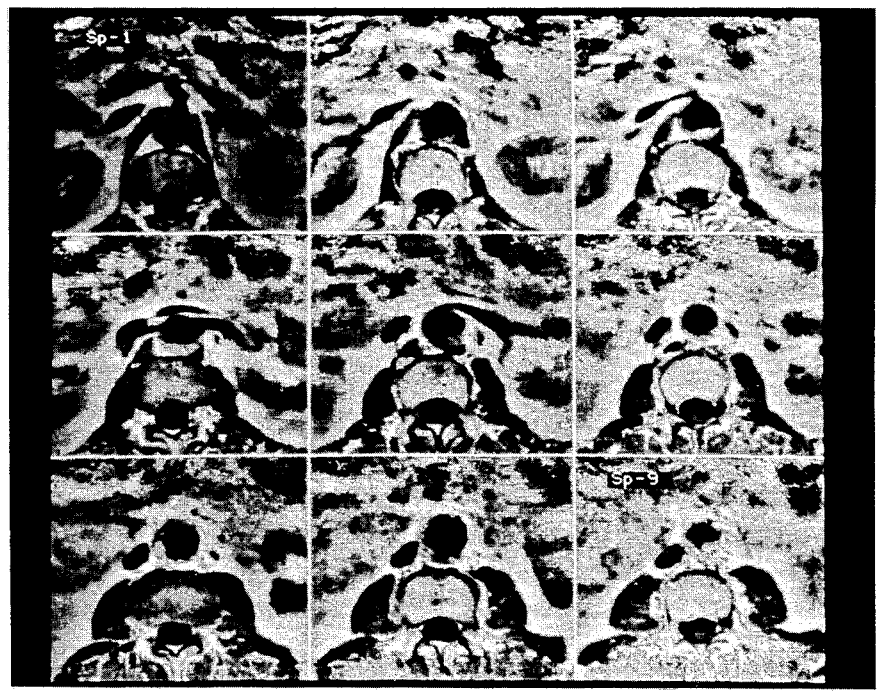
FIG. 5 shows a sequence of nine successive $T_1$ weighted images through the diseased aorta.

A complete set of $T_1$ weighted images through all 9 sections of the diseased vessel is shown in FIG. 5, which demonstrates the complexity of the changes in wall thickening. The same $T_1$ weighted pulse sequence parameters were used as in FIG. 4 for the diseased aorta.

In general, the lumen of a vessel appears dark with all pulse sequences due to spin washout, except in cases exhibiting significant flow artifact associated with the movement of the blood and the long $T_1$ of blood (approx. 1 sec, see W. G. Bradley, "Sorting out the Meaning of MRI Flow Phenomena", Diagnostic Imaging, vol. 9, no. 5, pp. 102-111, May 1987, for review). Flow artificats which can cause the lumen to appear bright are entry phenomenon and second echo rephasing. The lumen of most of the images in FIGS. 4 and 5 are dark compared to the surrounding vessel wall. However, the lumen appears gray in the $T_1$ weighted pulse sequence of the normal subject shown in FIG. 4, because, it is the first slice in the sequence (i.e., entry phenomenon).

The first major step in identifying and displaying the tissue types associated with the wall of the vessel is segmentation. Segmentation is required to delineate the wall of the aorta which will be classified (i.e., step 2 in FIG. 3). It is difficult to directly segment the aorta from the complex images shown in FIGS. 4 and 5 because no obvious and consistent distinguishing features of the aorta are visible in all slices.

Figure 6:
FIG. 6 shows segmentation of inner and outer wall for slice positions 5 (Sp-5) and 6 (Sp-6)

The segmentation of the wall of the aorta is completed in four steps which are summarized below and explained further later in this disclosure. (1) The approximate position of the aorta lumen in all slices is initially determined by utilizing a spot detector on a single "average" image. This "average" image is created by averaging the images from all slices together on a pixel by pixel basis. (2) A more accurate centroid of the lumen is then calculated for each slice utilizing a spot detector. The centroid of the lumen is determined as the peak of the spot detector output closest to the "average" centroid determined for all slices in (1) above. This process is required due to multiple significant spots which are generated when the spot detector is utilized on a single slice. (3) A region growing operation based on the centroid of the lumen provide the boundary of the lumen (i.e., inner boundary of the wall). A second region growing operation based upon the lumen boundary provides an approximate outer boundary of the wall of the aorta. (4) A boundary refining algorithm (Simplified Bead Chain Algorithm), utilizes the approximate outer boundary of the vessel wall as an initial plan to obtain a more accurate refined outer boundary. The results of this segmentation process, when applied to both the inner and outer walls of the diseased aorta, are shown in FIG. 6.

Reliable identification of the plaque constituent classes of normal wall (primarily smooth muscle), fatty lipid containing plaque, fibrous plaque (primarily connective tissue) and mixed complex plaque with regions of calcification in an excised aorta preparation are described above and in: M. B. Merickel, C. S. Carman, S. Ware, J. D. Pearlman, J. R. Brookeman, J. Mugler and C. Ayers, "Multidimensional MRI Pattern Recognition of Atherosclerosis", Proc. of the Eighth Annual Conference of the Engineering in Medicine and Biology Society, pp. 1142-1145, Nov. 1986. Simple pattern recognition classifiers, such as minimum distance to the means and Fisher linear classifiers, are sufficient for the identification using multidimensional image input consisting of $T_1$, pd and $T_2$ weighted image sequences. Johnson et al, Applied Multivariate Statistical Analysis, Prentice-Hall, 1982, pages 462-469. However, supervised classification techniques cannot be utilized in vivo due to the lack of appropriate a priori training data (i.e., histology). (Tou, J. T. and R. C. Gonzales, Pattern Recognition Principles, Reading, Mass.: Addison-Wesley Publishing Co., 1974. )

An unsupervised clustering technique for classification of the in vivo aorta images which requires no a priori information is used. ISODATA clustering algorithm is utilized due to its well known robustness and previous success in similar multidimensional problems as well as relative ease of implementation (Tou, J. T. and R. C. Gonzales, Pattern Recognition Principles, Reading, Mass: Addison-Wesley Publishing Co., 1974;

M. R. Anderberg, Cluster Analysis for Applications, San Francisco, Calif.: Academic Press, 1973; and G. H. Ball and J. D. Hall, ISODATA, A Novel Method of Data Analysis and Pattern Classification, Tech. Rep., Menlo Park, Calif.: Stanford Research Institute, 1965). ISODATA is a variation of the K-means clustering algorithm, in which data points are assigned to the nearest cluster (i.e., class). Distance in this case is measured as the Euclidean distance between the data point and cluster mean. ISODATA provides more flexibility than the K-means method because the number of clusters can be modified to fit the data more accurately. The algorithm consists of iterative splitting and merging of the clusters until the number of clusters remains constant. The number of clusters is increased by splitting of a cluster containing a single dimensional variance larger than a user selected threhold. The number of clusters is decreased by the merging of two clusters which are closer (measured by Euclidean distance) than a user selected threshold. There is also a provision for ignoring the data points which group into clusters with fewer than a user selected number of points. This last feature is used to remove wild points from the data analysis as they are identified.

Figure 7:
FIG. 7 shows a false color display and results of cluster analysis applied to the same two sections shown in FIG. 6.

With reference to FIG. 7, there is shown a false color display and results of cluster analysis applied to the same two sections shown in FIG. 6 using the ISODATA clustering algorithm. The false color display is created by loading the $T_1$, pd and $T_2$ weighted images into the red, green and blue image planes of the color imaging system to permit simultaneous viewing of all three pulse sequences. The inserts in the upper left hand corner of the upper images are the extracted vessel regions used for cluster analysis. Pseudo color display of cluster analysis result in the two lower images after classification of all pixels in the image based on clustering all pixels within the outer wall from all sections. The white lines circumscribe the inner and outer walls of all of the sections. Three different classes are recognized within the outer aorta wall: flowing blood in the aorta lumen; fatty plaque; and fibrous plaque.

ISODATA is applied to the entire region contained within the outer wall of the segmented aorta which includes both the wall and lumen. The input to ISODATA consists of the multidimensional $T_1$, pd and $T_2$ values of the regions for all of the imaged slices. Knowledge about the anatomy of the aorta is used to encourage the analysis to settle at an appropriate number of clusters. The cluster mean values from the clustering results is also used to classify the entire preprocessed images to produce a theme map as shown in FIG. 7. The clusters are labeled with a specific tissue type by comparing the clusters in the aorta wall with surrounding homogeneous tissues that are readily identifiable. The process of identifying different soft tissue types in the slices is significantly aided by the expert advice from radiologists familiar with the anatomy of the region. FIG. 7 demonstrates that the section of diseased aorta wall from the patient contains the 3 main tissue types of normal wall (i.e., smooth muscle, fatty plaque and fibrous tissue). No complex plaque or calcification were found in any of the slices from the diseased aorta studied in this specific case. Other studies demonstrate that complex plaque and particularly calcification (due to lack of signal), are readily visible in MRI images (M. B. Merickel, C. S. Carman, S. Ware, J. D. Pearlman, J. R. Brookeman, J. Mugler and C. Ayers, "Multidimensional MRI Pattern Recognition of Atherosclerosis", Proc. of the Eighth Annual Conference of the Engineering in Medicine and Biology Society, pp. 1142-1145, Nov. 1986.

Displaying the pattern recognition results described above in a direct manner that allows rapid manipulation is important. The rapid and effective display of 3-D structures is very dependent upon the underlying data structure utilized to represent the 3-D data. This is particularly true when it is desired to manipulate complex "real word" 3-D imagery rapidly.

Previously, the pattern recognition results in 3-D were displayed by extracting the contours of the different plaque constituents which are then utilized to create a wire frame model (M. B. Merickel, C. S. Carman, S. Ware, J. D. Pearlman, J. R. Brookeman, J. Mugler and C. Ayers, "Multidimensional MRI Pattern Recognition of Atherosclerosis", Proc. of the Eighth Annual Conference of the Engineering in Medicine and Biology Society, pp. 1142-1145, Nov. 1986 and M. B. Merickel, C. S. Carman, J. R. Brookeman, J. Mugler, M. F. Brown and C. Ayers, "Identification and 3-D Quantification of Atherosclerosis Using Magnetic Resonance Imaging." In Press, Computers in Biology and Medicine). The wire frame model is then tiled by mosaicing to create a solid model which could then be displayed utilizing high level solid modeling routines (e.g., MOVIE.BYU). The difficulty with this procedure is that it is time consuming and creates a 3-D model which does not always directly reflect the actual pattern recognition results. Extraction of the contours of the tissue regions identified by pattern recognition presents a particularly difficult problem because the tissue regions are not necessarily homogeneous and do not necessarily match regions in neighboring slices.

A 3-D display system which directly displays the pattern recognition results and is similar to the technique described by Farrell (E. J. Farrell, R. Zappulla and W. Yang, "Color 3-D Imaging of Normal and Pathologic Intracranial Structure", Computer Graphics and Applications, vol. 4, no. 9, pp. 5-17, Sept. 1983) is used by initially assigning a color to each tissue and then displaying each slice in the sequence in a frame by frame, back to front manner. The intensity of the color is modulated to produced depth shading in order to highlight the 3-D effect.

Data structures are used for representing the 3-D data in a compact manner which can be easily manipulated. The quadtree data structure for encoding the pattern recognition results as a sequence of 2-D quadtrees is a preferred one (A. Klinger and C. R. Dyer, "Experiments in picture representation using regular decomposition", Computer Graphics and Image Processing, vol. 5, pp. 68-105, Mar. 1976). This data structure is two dimensional in nature and is visualized as the recursive sub-division of a scene into quadrants such that the leaf nodes of the resulting tree represent an area of class homogeneity in the scene. This data structure is useful not only in the simplification of the display process, but also provides significant reduction in the amount of disk space required to store the sequence of frames of the classified object.

Given the thickness of each frame and the relative distance between the frames, a 3-D picture is constructed by displaying the frames from back to front, which facilitates hidden surface removal, and incorporating depth shading. Specifically, this is done by adding depth to each frame using the frame thickness information. Intuitively, the pixels in each frame are replicated to a given depth. However, the display software simply deals with the vertices of the quadrants, so that what takes place is the construction of a parallelpiped from the vertices the quadtree's root node. A geometric transformation is then applied to the eight vertices of the created parallel-piped. The transformation needs only to be applied at the root level due to the nature of the quadtree structure. Successive vertices are easily calculated from the vertices of the previous level. The visible faces of the transformed parallelpiped are also readily determined, so that the hidden faces do not need to be displayed (I. Gargantini, T. R. Walsh and O. L. Wu, "Viewing Transformations of Voxel-Based Objects via Linear Octress", Computer Graphics and Applications, vol. 6, no. 10, pp. 12–21, Oct. 1986).

The 3-D display system using a Lexidata graphics display station (LEX-90) configured with Solidview-M firmware. Using the Lexidata graphics station, display is then produced by recursively displaying each leaf node of the quadtree. Specifically, utilizing the Lexidata's Solidview-M firmware, the visible faces of a particular parallelpiped are displayed by sending the coordinates of the four vertices of each visible face, with the color intensity values for those vertices. The values for pixels within the face are interpolated within the Lexidata hardware.

With reference to FIG. 8, there is shown a perspective 3-D view of a diseased aorta. This is automatically produced by the apparatus previously described. In the top left of the Figure, there is a rotation of minus 25° around the x and y axis. The background is displayed in a light color and the fatty plaque is displayed by the lighter color in the figure. Slices 1–7 of the third quadrant have been removed to permit visualization of the interior of the aorta. The bottom left image is the same as the top left except there is shown fibrous tissue in the darker color, the top right image is a rotation of 25° around the x and y axes. Again with the background in a light color and the fatty plaque being shown in the lightest of the three shades on the inside of the vessel. Slices 1–7 of the second quadrant have been removed for better visualization. The bottom right image is the same as the top right except there is shown a fibrous tissue which is the darkest color shown on the wall of the vessels.

With reference to FIG. 9, is the same as FIG. 8 except for the omission of the background. The top left image shows a rotation of minus 25° around the x and y axis. Fatty plaque or lipid is shown and slices 1–5 of the third quadrant have been removed. The bottom left image is the same as the top left except for showing fibrous tissue in a darker shade. At the top right, the perspective is a rotation of 25° around the x and y axis. Fatty plaque or lipid is shown and slices 1–5 of the second quadrant have been removed. The bottom right image is the same as the top right except it shows, in addition to the lipid or fatty plaque, a fibrous tissue in the darker shading. The original images are in colors with the fibrous tissue in orange and the fatty plaque in yellow. These images are much more dramatic than the black and white used in the drawings.

Another valuable feature of the above 3-D display system is the ability to quantity the volume of the display tissues. Table 1 shows the volume of the aorta wall, fatty plaque and fibrous plaque which were displayed in FIGS. 8 and 9. Additionally, the volume of the plaque constituents is expressed as a percentage of the total wall volume. Lumenal narrowing was quantified by measuring the lumen cross sectional area at each slice position (Table 2). A definite decrease in cross sectional area is apparent in the middle slices.

| Tissue Type | Volume (ml) | Volume (%) |
| --- | --- | --- |
| Fatty Plaque | 6.9 | 37.7 |
| Fibrous Plaque | 6.5 | 32.7 |
| Normal Vessel Wall | 6.4 | 32.6 |

Table 1 above. Volume of each plaque constituent identified in diseased aorta. The volume of each component is also expressed as a percentage of the total wall volume.

| Slice | Lumen Cross Sectionl Area (mm$^2$) |
| --- | --- |
| 1 | 358 |
| 2 | 454 |
| 3 | 331 |
| 4 | 276 |
| 5 | 320 |
| 6 | 425 |
| 7 | 496 |
| 8 | 262 |

Table 2 above. Cross sectional area measurements through each of the eight slices of the diseased aorta. Note the lumenal narrowing which is particularly evident in the middle slices (Nos. 3–5).

Figure 10:
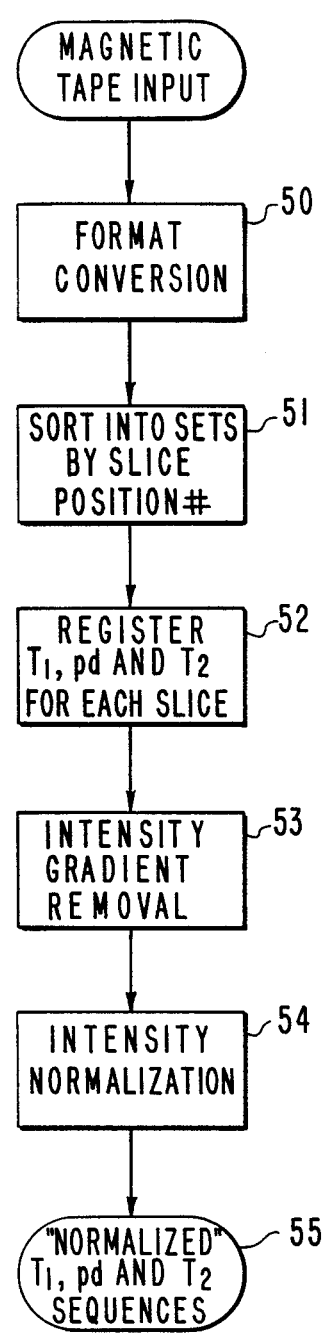
FIG. 10 shows a flow chart of the preprocessing sequence.

With reference to FIG. 10, there is shown a flow chart of the various steps for preprocessing of the information obtained as output from the MRI.

Complete sets of corresponding $T_1$, pd and $T_2$ imagery slices are written onto a standard 9 track magnetic tape at the MRI facility at a density of 1600 bits/inch. The tape is then transported to the Masscomp imagee processing/display computer and read onto the hard disk. The first step is format conversion 50 to convert the format of the image files into a standard format employed by the processing software (HIPL format; M. S. Lany, Y. Cohen and G. Sperling, "HIPS: A UNIX-based image processing system", Comp. Vision, Graphics and Image Processing, Vol. 24, pp. 331–347, 1984). The imagery is then sorted at Sort 51 into a $T_1$, pd and $T_2$ sequence of image files. The images in each sequence are sorted by slice position number and correspond to the same anatomical slice position for each sequence.

The corresponding pd and $T_2$ images for each slice position are then registered at Register 52 to the $T_1$ image, if they are not already registered. Such registration artifacts are typically due to errors in the reconstruction software of the MRI machine and need to be corrected. The misregistration consists of whole pixel x and/or y translation shifts. They are corrected by finding the peak in the cross correlation function for $T_1$ versus $T_2$ and $T_1$ versus pd (R. C. Gonzalez and P. Wintz, Digital Image Processing, Addison-Wesley Publishing Company, Reading, MA, 1987).

The raw MR images contain several artifacts which have to be removed before segmentation and classification can be performed. Most artifacts are caused by the use of the spine coil and are typical of surface coils currently employed in MRI imaging to increase the signal to noise ratio and spatial resolution. The sensitivity profile of the surface coil, such as the spine coil employed to image the aorta, causes the average intensity of the image to fall with distance from the center of the coil. This intensity fall of causes an intensity gradient to occur across the image of an individual slice as well as a reduction in average intensity of slices imaged further from the coil.

The intensity gradient within a slice is reduced at Intensity Gradient Removal 53 by employing the technique of dividing each image by a spatially smoothed copy of itself on a pixel by pixel basis as described by J. Hasselgrove and M. Prammer, "An Algorithm for Compensation of Surface-Coil Images for Sensitivity of the Surfac Coil", Magnetic Resonance Imaging, Vol. 4, pp. 469-472, 1986. The basic technique is modified by performing the calculation completely in the spatial domain. The low pass filtered image is calculated using a 21 pixel by 21 pixel overlapping averaging convolution filter. This technique significantly reduces the lower frequency surface oil intensity gradient and produces some high frequency emphasis which enhances the contrast of edges.

The average intensity of slices fall off with distance from the surface coil which required all of the slices belonging to each of the 3 pulse sequences to be normalized to one another. Intensity normalization 54 between slices is accomplished by identifying correspond regions in each image of at least one known tissue. One method for accomplishing this identification of known tissue regions is by using a K-means clustering procedure on the entire image with K set equal to some typically expected number of major tissues in the image (See J. T. Tou and R. C. Gonzalez, Pattern Recognition Principles, Addison-Wesley Publishing Company, Reading, MA, 1974 and M. R. Anderberg, Cluster Analysis for Applications, Academic Press, San Francisco, CA 1973). The K-means procedure computes the distance between each pixel and each of the K cluster centers, and associates that pixel with the cluster with the closest means, i.e., the smallest distance value. The distance measure used is the statistical distance (also known as the Mahalanobis distance) and is equivalent, in the one dimensional case, to dividing the squared Euclidean distance from the pixel to the cluster center by the variance of the cluster; $D_j = (x - x_j)^2 / \sigma_j$. Once all of the pixels have been assigned to a cluster, new cluster centers are computed to be the mean of all of the pixels in each cluster. Then the covariance matrix is computed for each cluster, and the inverse covariance matrix is also computed because it is needed to calculate the Mahalanobis distances. This K-means clustering algorithm repeats until either less than one percent of the pixels change cluster assignments in any one iteration, or until the maximum number of K-mean iterations, $I_k$, have been completed, where $I_k$ is set equal to a large value such as 20. At this point, the final set of clusters is written to a file, and the mean values of the clusters can be used to identify the tissue of interest, and to compute the required scale factor for normalization of that particular image to the entire set. This results in "Normalized" $T_1$, pd, and $T_2$ sequences 55 between slices.

The purpose of the segmentation process is to accurately determine the outer wall boundary of the vessel in all slices. The multidimensional $T_1$, pd and $T_2$ gray level values for the region within the outer wall then serves as input into the classification stage. The $T_1$ image sequence primarily represents structural information and most clearly defines the outer wall, and is therefore used as the input into the segmentation stage.

Figure 11:
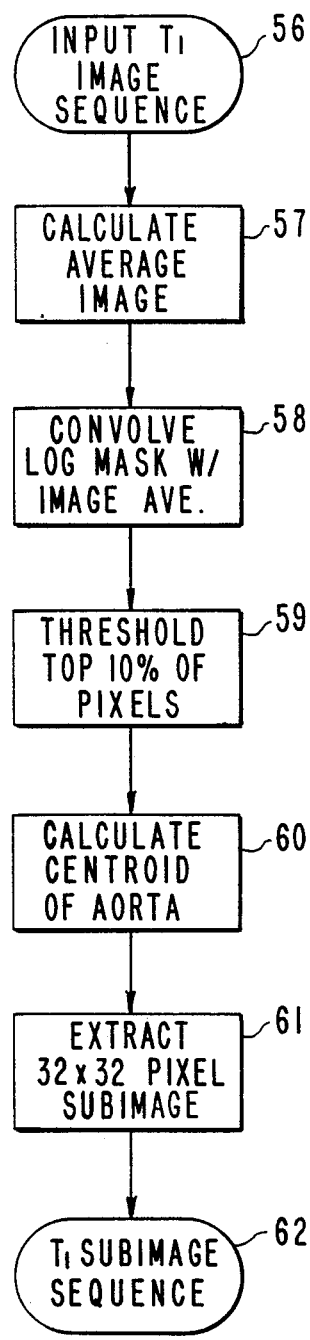
FIG. 11 shows a flow chart of the first stage of segmentation.

With referencee to the flow chart of FIG. 11, there is shown the first segmentation sequence.

The first step 56 in the segmentation process is therefore to obtain the preprocessed $T_1$ image sequence from FIG. 10. The second step 57 in the segmentation stage involves calculating a single average image from all $T_1$ slice position images. This average image is calculated in the following manner:

$$f_a(i,j) = \sum_{s=1}^{S} f_s(i,j)$$

where:
S = total number of slices
(i,j) = row (i) and column (j) index for pixel values
$f_s(i,j)$ = image for slice
$f_a(i,j)$ = average image The third step 58 is to convolve the average image with a Laplacian of a Gaussian (LOG) operator to enhance the spot corresponding to the lumen of the average vessel. The 21×21 pixel LOG convolution mask utilized for spot detection is shown below:

```
0 0 0 0 1 1 1 1 1 1 1 1 1 0 0 0 0 0 0
0 0 1 1 1 2 2 2 2 2 2 2 1 1 1 0 0 0 0
0 1 1 2 2 3 3 3 3 3 3 3 2 2 1 1 0 0 0
1 1 2 3 3 4 4 4 4 4 4 3 3 2 1 1 0 0
1 1 2 3 3 4 4 3 3 3 3 4 4 3 3 2 1 1 0
1 2 3 3 4 3 2 1 0 0 0 1 2 3 4 3 3 2 1 0
1 1 2 3 3 2 0 -2 -3 -4 -3 -2 0 2 3 4 3 2 1 1
1 2 3 4 4 2 0 -4 -9 -12 -9 -12 -9 -4 0 2 4 4 3 2 1
1 2 3 4 3 1 -2 -9 -13 -15 -16 -15 -13 -9 -2 1 3 4 3 2 1
1 2 3 4 3 0 -3 -12 -15 -21 -22 -21 -15 -12 -3 0 3 4 3 2 1
1 2 3 4 3 0 -4 -9 -16 -22 -24 -22 -16 -9 -4 0 3 4 3 2 1
1 2 3 4 3 0 -3 -12 -15 -21 -22 -21 -15 -12 -3 0 3 4 3 2 1
1 2 3 4 3 1 -2 -9 -13 -15 -16 -15 -13 -9 -2 1 3 4 3 2 1
1 2 3 4 4 2 0 -4 -9 -12 -9 -12 -9 -4 0 2 4 4 3 2 1
1 1 2 3 4 3 2 0 -2 -3 -4 -3 -2 0 2 3 4 3 2 1 1
1 2 3 3 4 3 2 1 0 0 0 1 2 3 4 3 3 2 1 0
1 1 2 3 3 4 4 3 3 3 3 4..4 3 3 2 1 1 0
1 1 2 3 3 4 4 4 4 4 4 3 3 2 1 1 0 0
0 1 1 2 2 3 3 3 3 3 3 3 2 2 1 1 0 0 0
0 0 1 1 1 2 2 2 2 2 2 2 1 1 1 0 0 0 0
0 0 0 0 1 1 1 1 1 1 1 1 1 0 0 0 0 0 0
```

The image resulting from the convolution operation is then thresholded at threshold step 59 to further localize the vessel. The top 10% (i.e., brightest) values are thresholded and saved for the average image sequence. The fifth step 60 is to calculate the centroid (center of mass) of the threshold region for the average slice. This centroid is then used as a central point for the Extract step 61 for extracting a 32 pixel by 32 pixel subimage from each $T_1$ slice which is centered about the centroid of the average slice. This results in a $T_1$ subimage sequence 62.

Figure 12:
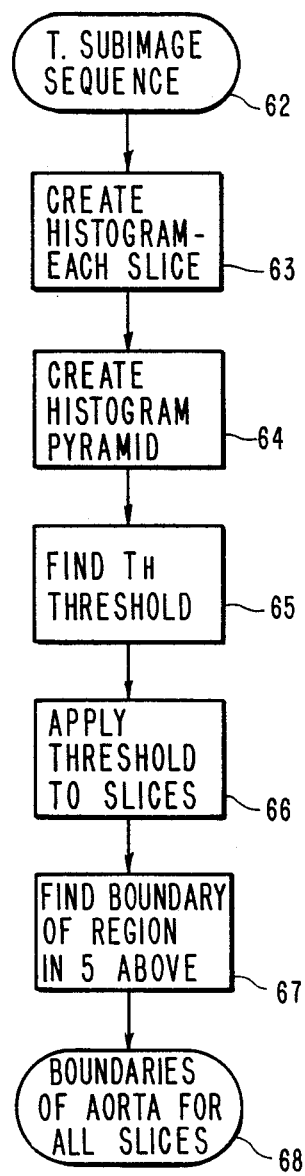
FIG. 12 shows a flow chart of the second stage of segmentation.
Figure 13:
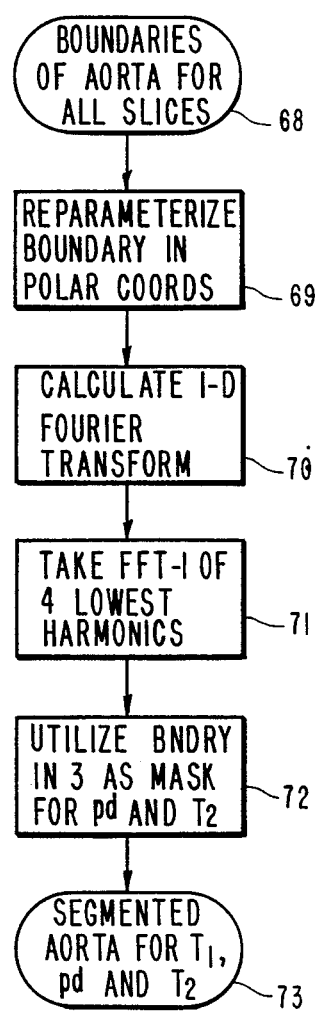
FIG. 13 shows a flow chart of the third stage of segmentation.

With reference to FIG. 12 there is shown the second sequence of steps in the segmentation routine.

Figure 14:
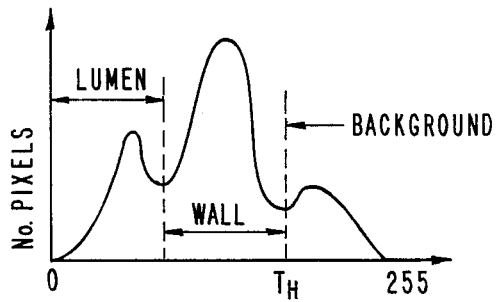
FIG. 14 shows a histogram created in FIG. 12.

The objective of the second set of segmentation steps is to extract the boundary of the outer wall of the vessel contained in the $T_1$ subimages. The first step 63 involves creating a histogram of each subimage slice as shown in FIG. 14, containing 255 gray level bins. It is desired to find the gray level threshold ($T_H$) between the background and wall in order to perform this segmentation step as shown in the histogram. However, the histogram is typically quite noisy which makes the determination of this threshold difficult.

A histogram pyramid 64 procedure is utilized to reduce the resolution of the histogram and enhance the determination of $T_H$. The histogram pyramid is created by performing a non-overlapping averaging process in which neighboring gray level bins are averaged together. In other words, gray level bins 0 and 1 are averaged together, followed by bins 2 and 3, bins 4 and 5, etc. This histogram pyramid procedure is repeated three (3) times, resulting in a final resolution of 32 gray levels. $T_H$ threshold 65 is then found as the second minimum gray level value in the low level histogram pyramid. This process is performed individually on each $T_1$ subimage slice.

The inner region of the vessel is found by applying the threshold value $T_H$ at 66 found at 65 to the corresponding subimage. The threshold $T_H$ is applied to each subimage by finding all pixels in the subimage whose gray level value is less than $T_H$. The result of this process is schematized in FIG. 14A which shows the interior of the vessel region surrounded by background which has been set to gray level value of 0. An estimate of the boundary of the outer wall of the vessel is found by tracing or following the contour of the extracted region.

The boundary of region step 67 which is extracted at this stage typically has artifacts which must be reduced. These artifacts take the form of extraneous regions which do not belong to the interior of the vessel. Such an extraneous region is shown as "Garbage" in FIG. 14A as a jut or outcropping of the vessel wall which corresponds to a tissue not associated with the vessel wall. Thus, Segmentation Number 2 of FIG. 12 results in boundaries of the aorta for all slices at 68.

The objective of the third set of segmentation steps is to significantly reduce or remove the extraneous juts or outcroppings of the vessel wall which have resulted from the application of the thresholding process described in the above second set of segmentation steps. This "cleaning up" processes is performed by reparameterizing the boundary of the extracted regions at 69. The first step in this reparameterization process is to calculate the centroid of the extracted region (not boundary) for each slice position. Calculations of the centroid based on all the points in the region (rather than just boundary points) minimizes the contributions from the extraneous juts and outcroppings which must be removed.

Figure 14A:
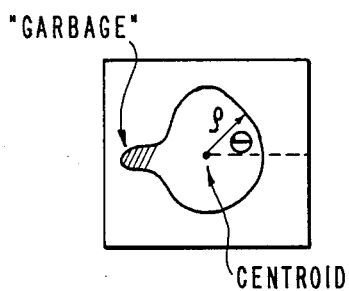
FIG. 14A shows a schematized example of a aorta boundary created in FIG. 12.
Figure 15:
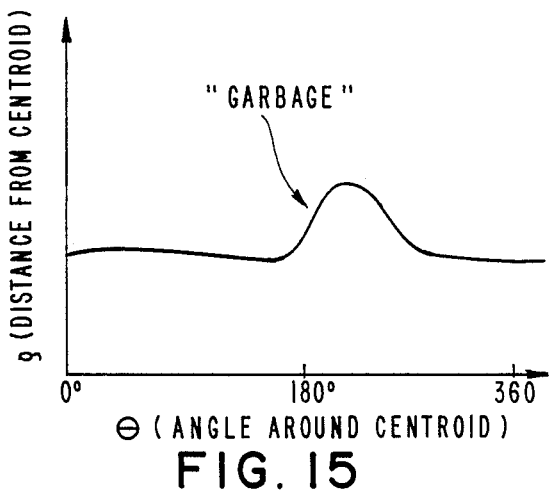
FIG. 15 shows a plot of the reparameterized boundary of FIG. 12.

The boundary determined in Segmentation Number 2 for each slice position is then reparameterized into polar coordinates 69 with respect to the respective centroids calculated in the above paragraph. The reparameterization process involves expressing each boundary point in the polar coordinate form of rho and theta, where rho is the distance of the boundary point from the centroid and theta is the angle of the point about the centroid as shown in FIG. 14A. FIG. 15 shows a schematized example of the reparameterized boundary shown in FIG. 14A.

The reparameterization of each of the outer wall boundaries into polar coordinate form permits each of these boundaries to be described by a 1-D Fourier Transform 70 to permit the boundary to be described by a Fourier Descriptor (see C. C. Lin and R. Chellapa, "Classification of Partial 2-D Shapes Using Fourier Descriptors", I.E.E.E. Transactions on Pattern Analysis and Machine Intelligence, Vol. PAMI-9 No. 5), pp. 686–690, 1987). A 1-D Fourier Transform is calculated for each boundary point utilizing theta as the independent variable and rho as the dependent variable (see FIG. 15). This process is repeated for the polar coordinate parameterized boundary of each slice position.

The boundary for each slice position is reconstructed utilizing only the first four (4) lowest frequency harmonics of the Fourier Transform 71. The reconstructed boundary is considerably smoother than the original boundary and does not exhibit the extraneous "garbage" of juts and outcroppings.

The new boundaries circumscribe the desired outer wall of the vessel for each slice position. These new boundaries are then utilized as mask at 72 for extracting the vessel regions from the $T_1$, pd and $T_2$ normalized images for each slice position. The output of the segmentation process 73, therefore, consists of $T_1$, pd and $T_2$ gray level image sequences. The images in each sequence are 32 pixels by 32 pixels in which the vessel region contains the appropriate gray level and the background surrounding the vessel is set to gray level value of 0. These three (3) image sequences are the input to the following classification procedures.

FIG. 16 contains a flow chart of the classification stage of this system. The first part consists of applying our unsupervised cluster analysis program to the pixels within the region identified by the segmentation process. This program proceeds to find the natural groupings or pixel clusters in an image set. To do this it uses a criterion, called the CAIC, which measures the goodness of fit of the clusters to the data at each iteration to guide the decisions within the program. The CAIC is an information theoretic criterion which specifically measures the negative entropy of the K clusters taken as a whole with a penalty added which is proportional to the number of parameters which were estimated from the input data. In the present case 9 parameters are estimated for each cluster, 3 in the mean vector and 6 in the covariance matrix (see H. Akaike, "A New Look at the Statistical Model Identification", I.E.E.E. Trans. on Automatic Contrl, Vol., AC-19 (No. 6), pp. 716–723, 1974 and H. Bozdogan, "Multi-Sample Cluster Analysis as an Alternative to Multiple Comparison Procedures", Bulletin Info. Cyber. Vol. 22 (No. 1–2) pp. 95–130, 1986). A small CAIC value indicates a better fit of the clusters to the data.

Figure 18:
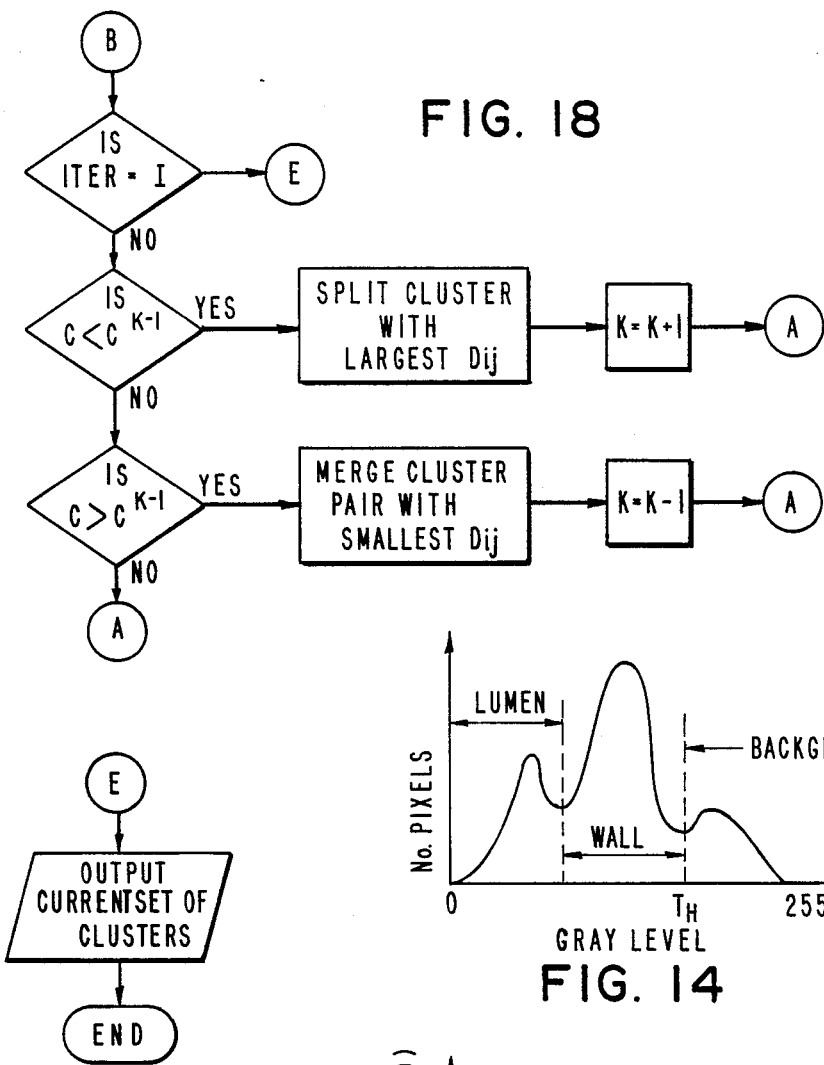

The program proceeds as follows (referring to the flow chart in FIGS. 17 and 18). First, the intensity values from the set of images ($T_1$, pd and $T_2$) for all of the pixels in the segmented vessel region from all of the slices are read into a multi-dimensional array (one dimension for each image in a slice) 79. The global variables are then initialized 80, including the $C^k$ array, which will contain the minimum CAIC value when there are K clusters, and Cmin, which will contain the global minimum CAIC value, and which are initially set equal to a very large number. The current number of clusters, K, and the iteration counter, iter, are set equal to one (1).

The first iteration of the algorithm is then started by calling a procedure to perform a K-means clustering of the data 81 (see J. S. Tou and R. C. Gonzalez, Pattern Recognition Principles, Addison-Wesley Publishing Company, Reading, MA, 1974 and M. R. Anderberg, Cluster Analysis for Applications, Academic Press, San Francisco, CA, 1973). This procedure computes the distance between each pixel and each of the K cluster centers, and associates that pixel with the cluster with the closest mean, i.e., the smallest distance value. The distance measure used is the statistical distance (also known as the Mahalanobis distance) and is equivalent, in the one dimensional case, to dividing the square Euclidean distance from the pixel to the cluster center by the variance of the cluster; $D_j=(x-x_j)^2/\sigma_j$. Once all of the pixels have been assigned to a cluster, new cluster centers are computed to be the mean of all of the pixels in each cluster. Then the covariance matrix is computed for each cluster, and the inverse covariance matrix is also computed becausee it is needed to calculate the Mahalanobis distances. This K-means clustering algorithm repeats until either less than one percent of the pixels change cluster assignments in any one iteration; or until the maximum number of K-means iterations, $I_k$, have been completed, where $I_k$ is set equal to two (2).

After the K-means clustering procedure has finished, all of the clusters are examined to see if they are sufficiently large for continued processing. If any of the clusters has a number of pixels, $n_j$, less than one percent of the total number of pixels in the analysis, N, then the cluster is removed. When a cluster is removed, all of the pixels associated with that cluster are marked as wild points, they are made unavailable for further use by the program, and the number of clusters, k, is decremented by one (1).

At this point the CAIC value is computed and stored in the variable C. Because a smaller CAIC value is better, the program searches for the globally smallest value of the CAIC. This is accomplished by the bottom 4 decisions in the flow chart in FIG. 17 and the middle 2 decisions in the flow chart of FIG. 18. The first and third decisions, test 1 and 2, determine if the program is repeating cluster sets it has been through already, and the decisions in FIG. 18 determine if the number of clusters should be increased or decreased for the next iteration. Test 1, $C>C^k$ and $C^k<>C_{MIN}$ and $C-C^k<0.01$, determines if the current CAIC value, C, is greater than the minimum value when there were K clusters, $C^k$, if this minimum value is not equal to the global minimum, $C_{MIN}$, and if the difference between the current value and the minimum value when there were K clusters if less than 1.0 percent. If test 1 is true, than the program is repeating itself and it exits the main loop. The next test determines if the current value, C, is less than the minimum value when there were K clusters, $C^k$, and updates this minimum if the current value is less. Test 2, $C>C_{MIN}$ and $C-C_{MIN}<0.001$, is similar to test 1, except that it compares the current value, C, with the global minimum value, $C_{MIN}$, and includes a stricter test of their difference, with the cutoff set at 0.1 percent instead of 1.0 percent. If this test is true than the program is covering old ground and it also exits the main loop. The last decision in FIG. 17 checks to see if the global minimum value, $C_{MIN}$, should be updated or not, and updates it if the current value is less than the global minimum. If the global minimum value is updated, then a copy of the state of the program is made, including the value of K and the contents and definitions of each of the K clusters. At this point, the first decision on the flow chart of FIG. 18, iter is checked to see if it has been running too long, if the current iteration count equals the maximum number of iterations, I set equal to 40, and if so, exit the loop.

The next decision determines whether K should be increased. If the current CAIC value, C, is less than the minimum value when there were one less number of clusters, $C^{k-1}$, then one of the current clusters is split into two. The cluster which is split is the one with the largest variance element in its covariance matrix, $\sigma_{jmax}$. The split is performed by computing two new cluster centers, one on either side of the cluster center to be split, and the pixels of the cluster are divided between the two halves according to which center the pixels are closest to. The two new cluster means and covariances are computed, and the program loops back to the K-means clustering procedure, incrementing the iteration counter, iter, by one (1). If the decision was not to increase K, then the program checks whether to decrease K. If the current CAIC value, C, is greater than the minimum value when there was one less number of clusters, $C^{k-1}$, than the closet pair of clusters is merged. This pair of clusters is found by computing the statistical distance between all of the possible combinations of pairs of clusters, $D_{ij}$, and combining the clusters with the smallest distance value. The clusters are merged by computing a new cluster center as the average of the two cluster centers, and the covariance matrix likewise. Then also the program loops back to the K-means clustering procedure, incrementing the iteration counter, iter, by one (1). If K is neither increased or decreased then we loop back to the K-means clustering procedure, also incrementing the iteration counter, iter, by one (1). Finally, when the program exits the main loop, it takes the copy it made of the best set of clusters and writes it out to a file.

In the second step of the process diagrammed in FIG. 16, the vessel pixels in the segmented image are classified 75 with the above best set of clusters using a well studied supervised classifier. Specifically, the classifier is a Fisher Linear Classifier (see R. A. Johnson and D. W. Wichern, Applied Multivariate Statistical Analysis, Prentice Hall, Inc., Englewood Cliffs, NJ, 1982) which performs air wise tests encompassing all pairs of input clusters, assigning the pixel to the cluster which in all of its paired test is the closest of the pair to the pixel.

The third step 76 in the process is to label the above best set of clusters using another supervised classifier. Each cluster is labeled with the tissue class name of the tissue cluster it is closest to using the Mahalanobis distance measure. It is at this stage that information about the characteristics of MR images of soft tissues is used in the definitions of the tissue class clusters. It is currently performed on a case by case basis by radiologist examining both the clustering results and the original MR images. These labeling results are used to modify the results of the cluster analysis, effectively combining several of the best set of clusters into a smaller set of relevant classes. And the last step 77 in FIG. 16 involves labeling the vessel pixels by assigning to them the label now associated with their respective cluster. This gives a sequence of tissue maps 78.

FIG. 19 shows a flow chart of the 3-D quantification and display stage of the system. The first step 82 consists of converting the format of the classification result from a 2 dimensional array of tissue classe into a quadtree. This process involves starting with the input image as the active area, and recursively subdividing the active area into four quadrants, making each the active area in turn, until the active area consists of a homogeneous region, i.e., all pixels in the region have the same value. At this point, the value of the pixels in the region are stored in a leaf node of the quadtree data structure and the next quadrant is made the active area until all quadrants have been examined. In the second step 83 this quadtree formatted data is processed by a program which computes the volumes of each tissue type and the cross-sectional areas of each tissue in each slice. The volume measurements are then combined with the total volume of the vessel minus the lumen volume to give the percentage volume of each tissue in the vessel wall, and the cross-sectional area measurements are combined with the cross-sectional area of the vessel in each slice to give the percentage constriction at each slice.

The 3-D display program, using the quadtree data as input, allows the user to specify any rotation, scaling, and translation (RST transformation) of the 3-D object for display, and the program will generate the appropriately shaded display as the user waits. Because the quadtree is a hierarchical structure the program only has to apply the RST transformation once, to the root node of the tree, and the transformed positions of the quadrants can be computed from their parent's position. The display program also makes use of the surface shading and hidden surface removal capabilities of the Lexidata display device, sending it only the 4-D values for the vertices (x, y, z and intensity) of each of the faces that are visible for each leaf node in the quadtree. (A leaf node in a quadtree corresponds to one or more pixels in the original image.) The user is also able to select a quadrant to be removed from the display so that hidden objects can be made visible in a standard way. Thus, the 3-D displays 84 of the invention are created.

There is thus described an image processing, pattern recognition and 3-D graphical display system and method that permits a noninvasive evaluation of atherosclerosis using MRI imagery. This approach is specifically applied to the evaluation of atherosclerosis in the abdominal aorta of a patient in vivo. A key concept to this approach is the determination of both structural and functional information from the multidimensional imagery which is not available with a sequence of imagery generated with a single pulse sequence. These techniques are essential to exploiting the tremendous amount of information available in new biomedical imaging modalities, such as MRI.

Several problems unique to the in vivo environment are addressed. A particularly difficult problem is relating the relative image intensity values observed in one patient to other patients without the aid of "absolute" information regarding the signature of different tissues. This problem is solved by application of an unsupervised classifer such as ISODATA. Such an unsupervised classifier is able to effectively determine the number of clusters in the data, but still requires that the cluster be labeled as a specific tissue type using a priori information, such as provided by radiologist.

The ability to reliably and noninvasively quantify the display the different tissue components associated with atherosclerosis provided by the present invention is important to the early detection of the disease in high risk, asymptomatic patients. This imaging system of the invention also provides a means of directly assessing the effectiveness of various therapies, such as drug, exercise and dietary plaque constituents over time. Additionally, the ability to measure the volume of these plaque constituents in vivo provides a means of staging the disease process to more accurately measure its time course and response to intervention.

While the invention has been described using MRI for the input data and is particularly directed to atherosclerosis, many aspects of the invention are useable with other noninvasive input data such as positron emission tomography (PET) and ultrasound scans and is also useable for other tissue such as breast scans.

While a preferred embodiment of the invention has been shown and described, it will be understood that there is no intent to limit the invention by such disclosure but rather it is intended to cover all modifications and alternative constructions falling within the spirit and scope of the invention as defined in the appended claims.

What is claimed is:

1. A noninvasive imaging system for the display of a mammalian soft tissue live body part such as blood vessels or similar soft tissue for evaluation of soft tissue, using information obtained from multiple sequenced image slices produced by a body scan such as MRI and PET comprising:
   an electronic digital storage means for storing said information;
   a computer processing means for processing said information from said storage means;
   a graphics display station means for displaying an image resulting from said processed information;
   said computer processing means including:
   means for determining the boundary of said soft tissue body part from said image slices;
   means for extracting said soft tissue body part;
   means for clustering and determining the different soft tissue types of interest in said body part; and
   means for creating a data base for said extracted soft tissue body part including the different soft tissue types with their location and volume for displaying in contrasting delineation on said graphics display station whereby said display shows an extracted view of said body part with said different soft tissues shown delineated in their volumetric quantities and shape at the correct location in said body part.

2. The noninvasive imaging system of claim 1, wherein said image slices are is made by an MRI and each of said image slices is a set of images one of which is produced by $T_1$ emphasis.

3. The noninvasive imaging system of claim 2, wherein each of said images in said image slice sets are brought into registration with one another prior to determining the boundary of said body part.

4. The noninvasive imaging system of claim 3, wherein:
   said MRI scan utilizes a surface intensity coil for increasing the signal to noise ratio and improving the spatial resolution; and
   said noninvasive imaging system includes means for reducing the intensity gradient created by said surface intensity coil.

5. The noninvasive imaging system of claim 4, wherein means included for normalizing the intensity between each of said images in each of said image slice sets.

6. The noninvasive imaging system of claim 5, wherein means are provided for calculating a single average image from all of said images produced by $T_1$ emphasis.

7. The noninvasive imaging system of claim 6, wherein means are provided to convolve said average image by using a convolution mask.

8. The noninvasive imaging system of claim 7, wherein means are provided for thresholding the brightest values of said convolved image.

9. The noninvasive imaging system of claim 8, wherein means are provided for producing the centroid of said thresholded convolved image.

10. The noninvasive imaging system of claim 9, wherein means are provided for extracting a subimage from each of said $T_1$ emphasized image slices by using said centroid as a central point with said subimages being large enough to include said body part.

11. The noninvasive imaging system of claim 10, wherein means are provided for determining the approximate boundary of said body part by first creating a histogram of each of said subimage slices followed by producing a threshold analysis to determine said approximate boundary.

12. The noninvasive imaging system of claim 11, wherein means are provided for removing artifacts from said approximate boundary and reconstructing the boundary into a new boundary.

13. The noninvasive imaging system of claim 12, wherein means are provided for extracting the body part of interest from each slice by utilizing said new boundary as a mask.

14. The noninvasive imaging system of claim 1, wherein means are provided for classification which utilizes unsupervised analysis of said body part by finding the natural groupings or pixel clusters in said image slices.

15. The noninvasive imaging system of claim 14, wherein means are provided for carrying out said unsupervised analysis by use of CAIC criterion and assignment of each pixel with a cluster which has the closest Mahalanobis distance.

16. The non-invasive imaging system of claim 15, wherein means are provided for removing all pixels from further consideration which are assigned to clusters insufficiently large.

17. The noninvasive imaging system of claim 16, wherein means are provided for merging and splitting pixel clusters until the best set of clusters are found.

18. The noninvasive imaging system of claim 17, wherein means are provided for labelling each cluster with its tissue class name; labelling each pixel by assigning to them the label now associated with their respective cluster and using said labeled pixels to form a sequence of tissue maps.

19. The noninvasive imaging system of claim 1, wherein means are provided for labeling the pixel in each of said image slices with its tissue class and using said labeled pixels to form a sequence of tissue maps.

20. The noninvasive imaging system of claim 19, wherein means are provided for determining the volumes of each tissue type.

21. The noninvasive imaging system of claim 20, wherein said tissue type volumes are determined by using a quadtree data structure.

22. The noninvasive imaging system of claim 20, wherein means are provided for determining the cross-sectional areas of each tissue in each slice.

23. A method for noninvasive display of a mammalian soft tissue live body part using information obtained from multiple image slices produced by a body scan such as MRI and PET comprising the following steps:
produce multiple sequenced image slices by noninvasively scanning a mammalian body;
segment the entire scene represented by the image slices and identify the boundary of said soft tissue body part;
extract said body part by extracting a region enclosed within said boundary;
cluster the different soft tissue types of interest in said soft tissue body part; and
create a data base for the different soft tissue types including their location and volume in contrasting delineation for displaying on a graphics display station whereby said display shows an extracted view of said body part with said different soft tissues shown delineated in their volumetric quantities and shape at the correct location in said body part.

24. The noninvasive 3-D display method of claim 23, wherein said body scan is made by MRI and the production of each of said images slices includes production of a set of images one of which is produced by $T_1$ emphasis.

25. The noninvasive 3-D display method of claim 24, which includes the steps of bringing into registration each of said images in said image slice sets with one another prior to determining the boundary of said body part.

26. The noninvasive 3-D display method of claim 25, which includes the the steps of making said MRI scan utilizing a surface intensity coil for increasing the signal to noise ratio and improving the spatial resolution; reducing the intensity gradient created by said surface intensity coil.

27. The noninvasive 3-D display method of claim 26, which includes the step of normalizing the intensity between each of said images in each of said image slice sets.

28. The noninvasive 3-D display method of claim 27, which includes the step of calculating a single average image from all of said images produced by $T_1$ emphasis.

29. The noninvasive 3-D display method of claim 28, which includes the step of convolving said average image by using a convolution mask.

30. The noninvasive 3-D display method of claim 29, which includes the step of thresholding the brightest values of said convolved image.

31. The noninvasive 3-D display method of claim 30, which includes the step of producing the centroid of said thresholded convolved image.

32. The noninvasive 3-D display method of claim 31, which includes the step of extracting a subimage from each of said $T_1$ emphasized image slices by using said centroid as a central point with said subimage being large enough to include said body part.

33. The noninvasive 3-D display method of claim 32, which includes the steps of determining the approximate boundary of said body part by first creating a histogram of each of said subimage slices followed by making a threshold analysis to determing said approximate boundary.

34. The noninvasive 3-D display method of claim 33, which include the steps of removing artifacts from said approximate boundary and reconstructing the boundary into a new boundary.

35. The noninvasive 3-D display method of claim 34, which includes the step of extracting the body part of interest from each slice by utilizing said new boundary as a mask.

36. The noninvasive 3-D display method of claim 23, which includes the step of extracting from said slices said body part of interest.

37. The noninvasive 3-D display method of claim 36, which includes the step of classification utilizing the unsupervised analysis of said body part by finding the natural groupings or pixel clusters in said image slices.

38. The noninvasive 3-D display method of claim 37, which includes the step of carrying out said unsupervised analysis by use of CAIC criterion and assignment of each pixel with a cluster which has the closest Mahalanobis distance.

39. The noninvasive 3-D display method of claim 38, which includes the step of removing all pixels from further consideration which are assigned to clusters insufficiently large.

40. The noninvasive 3-D display method of claim 39, which includes the steps of merging and splitting pixel clusters until the best set of clusters are found.

41. The noninvasive 3-D display method of claim 40, which includes the steps of labelling each cluster with its tissue class name; labelling each pixel by assigning to them the label now associated with their respective cluster and using said labeled pixels to form a sequence of tissue maps.

42. The noninvasive 3-D display method of claim 37, which includes the steps of labeling the pixel in each of said image slices with its tissue class and using said labeled pixels to form a sequence of tissue maps.

43. The noninvasive 3-D display method of claim 42, which includes the step of determining the volumes of each tissue type.

44. The noninvasive 3-D display method of claim 43, which includes the step of determining by said tissue type volumes using a quadtree data structure.

45. The noninvasive 3-D display method of claim 44, which includes the step of determining the cross-sectional areas of each tissue in each slice.

46. A noninvasive imaging system for the 3-D display of atherosclerosis of a living human blood vessel using information obtained from multiple image slices produced by a MRI body scan comprising:
an electronic digital storage means for storing said information;
a computer processing means for processing said information from said storage means;
a graphics display station means for displaying a 3-D image resulting from said processed information;
said computer processing means including:
means for taking multiple sequenced image slice sets wherein each set includes three images representing proton emphasis, $T_1$ emphasis and $T_2$ emphasis and normalizing the images so that they represent a common intensity,
means for segmenting said normalized image for delineating the boundary of and extracting said living human blood vessel;
classification means for using unsupervised clustering with no a priori knowledge to define the label lipid tissue, fibrous tissue and calcified tissue and assign different colors to each tissue; and
means for creating a 3-D data base for the tissue types including their location and volume in different colors for displaying on said graphics display stations whereby said display shows a 3-D extracted view of the vessel with said lipid tissue, fibrous tissue and calcified tissue, to the extent present, shown in different colors in their volumetric quantities and shape at the correct location in said vessel.

47. The noninvasive imaging system of claim 46, wherein means are included for bringing each of said images in said image slice sets into registration with one another prior to determining the boundary of said body part.

48. The noninvasive imaging system of claim 47, wherein:
said MRI scan utilizes a surface intensity coil for increasing the signal to noise ratio and improve the spatial resolution; and
means are included for reducing the intensity gradient created by said surface intensity coil.

49. The noninvasive imaging system of claim 48, wherein means are provided for normalizing the intensity between each of said images in each of said image slice sets.

50. The noninvasive imaging system of claim 49, wherein means are provided for calculating a single average image from all of said images produced by $T_1$ emphasis.

51. The noninvasive imaging system of claim 50, wherein means are provided to convolve said average image by using a convolution mask.

52. The noninvasive imaging system of claim 51, wherein means are provided for thresholding the brightest values of said convolved image.

53. The noninvasive imaging system of claim 52, wherein means are provided for producing the centroid of said thresholded convolved image.

54. The noninvasive imaging system of claim 53, wherein means are provided for extracting a subimage from each of said $T_1$- emphasized imaged slices by using said centroid as a central point with said subimages being large enough to include said body part.

55. The noninvasive imaging system of claim 54, wherein means are provided for determining the approximate boundary of said body part by first creating a histogram of each of said subimage slices followed by producing a threshold analysis to determine said approximate boundary.

56. The noninvasive imaging system of claim 55, wherein means are provided for removing artifacts from said approximate boundary and reconstructing the boundary into a new boundary.

57. The noninvasive imaging system of claim 56, wherein means are provided for extracting the body part of interest from each slice by utilizing said new boundary as a mask.

58. The noninvasive imaging system of claim 46, wherein means are provided for carrying out said unsupervised clustering by use of CAIC criterion and assignment of each pixel with a cluster which has the closest Mahalanobis distance.

59. The non-invasive imaging system of claim 58, wherein means are provided for removing all pixels from further consideration which are assigned to clusters insufficiently large.

60. The noninvasive imaging system of claim 59, wherein means are provided for merging and splitting pixel clusters until the best set of clusters are found.

61. The noninvasive imaging system of claim 60, wherein means are provided for labelling each cluster with its tissue class name; labelling each pixel by assigning to them the label now associated with their respective cluster and using said labeled pixels to form a sequence of tissue maps.

62. The noninvasive imaging system of claim 61, wherein means are provided for determining the volumes of each tissue type.

63. The noninvasive imaging system of claim 62, wherein said tissue type volumes are determined by using a quadtree data structure.

64. The noninvasive imaging system of claim 63, wherein means are provided for determining the cross-sectional areas of each tissue in each slice.

* * * * *